US012797618B2

(12) United States Patent
Mech

(10) Patent No.: US 12,797,618 B2
(45) Date of Patent: Nov. 17, 2026

(54) NEUROMODULATION AND OTHER THERAPIES TO TREAT A COMBINATION OF OBSTRUCTIVE SLEEP APNEA AND CENTRAL SLEEP APNEA

(71) Applicant: The Alfred E. Mann Foundation for Scientific Research, Valencia, CA (US)

(72) Inventor: Brian Vernon Mech, Buffalo, MN (US)

(73) Assignee: The Alfred E. Mann Foundation for Scientific Research, Valencia, CA (US)

(*) Notice: Subject to any disclaimer, the term of this patent is extended or adjusted under 35 U.S.C. 154(b) by 394 days.

(21) Appl. No.: 18/534,427

(22) Filed: Dec. 8, 2023

(65) Prior Publication Data

US 2024/0207615 A1 Jun. 27, 2024

Related U.S. Application Data

(60) Provisional application No. 63/476,877, filed on Dec. 22, 2022.

(51) Int. Cl.
*A61N 1/36* (2006.01)
*G16H 50/20* (2018.01)

(52) U.S. Cl.
CPC ........ *A61N 1/36135* (2013.01); *A61N 1/3611* (2013.01); *A61N 1/36167* (2013.01); *G16H 50/20* (2018.01); *A61N 1/36053* (2013.01)

(58) Field of Classification Search
None
See application file for complete search history.

(56) References Cited

U.S. PATENT DOCUMENTS 7,636,600 B1 * 12/2009 Koh .................. A61N 1/36564 607/42
11,464,977 B2 10/2022 Schulhauser et al.
(Continued)

FOREIGN PATENT DOCUMENTS

WO 2021/242633 A1 12/2021
WO 2022/020489 A1 1/2022

OTHER PUBLICATIONS

Ben Salah et, al., "Hypoglossal Nerve Stimulation in the Treatment of Obstructive Sleep Apnea", 2017 14th International Multi-Conference on Systems, Signals & Devices (SSD), IEEE, XP033276740, Mar. 28, 2017, pp. 429-433.
(Continued)

*Primary Examiner* — Mallika D Fairchild
(74) *Attorney, Agent, or Firm* — ARENTFOX SCHIFF LLP

(57) ABSTRACT

The present disclosure generally relates to systems and methods for stimulating the hypoglossal nerve (HGN) and phrenic nerve (PN) to treat OSA and CSA for a subject. The system includes an implantable pulse generator (IPG) coupled to a first electrode and a second electrode, where the first electrode is configured to stimulate a HGN of the subject and the second electrode is configured to stimulate a PN of the subject. The system does not require the detection and classification of an apneic event or hypopnea event, but rather commands a first electrode to stimulate the HGN to treat OSA and commands a second electrode to deliver an inspiration stimulation signal to stimulate the PN for treating CSA by driving a respiration pace for the subject. The first electrode is commanded to deliver the stimulation signal to stimulate the HGN according to the respiration pace driven by the inspiration stimulation signal.

20 Claims, 7 Drawing Sheets

(56) References Cited

U.S. PATENT DOCUMENTS

| | | | | |
|---|---|---|---|---|
| 2015/0283383 A1* | 10/2015 | Ternes | A61N 1/3962 | |
| | | | 607/42 | |
| 2020/0147376 A1* | 5/2020 | Dieken | A61N 1/36139 | |
| 2021/0290957 A1* | 9/2021 | Schulhauser | A61B 5/318 | |
| 2023/0095780 A1* | 3/2023 | Rondoni | A61B 5/4818 | |
| | | | 600/301 | |

OTHER PUBLICATIONS

International Search Report and Written Opinion received for PCT Patent Application No. PCT/US2023/083380, mailed on Apr. 2, 2024, 14 pages.

Kezirian et al., Electrical Stimulation of the Hypoglossal Nerve in the Treatment of Obstructive Sleep Apnea, Sleep Medicine Reviews, W.B. Saunders, Amsterdam, NL, Oct. 1, 2010, 14(5):299-305.

Han et al., "Data Mining: Concepts and Techniques" Second Edition, The Morgan Kaufmann Series in Data Management Systems, 2006, 770 pages.

Kamiński et al., "A framework for sensitivity analysis of decision trees", Central European Journal of Operations Research, vol. 26, 2018, pp. 135-159.

Karimi et al., "Generation and Interpretation of Temporal Decision Rules", International Journal of Computer Information Systems and Industrial Management Applications, vol. 3, 2011, pp. 314-323.

Prinzie et al., "Random Multiclass Classification: Generalizing Random Forests to Random MNL and Random NB", R. Wagner, N. Revell, and G. Pernul (Eds.): DEXA 2007, LNCS 4653, 2007, pp. 349-350.

Denisko et al., "Classification and interaction in random forests", PNAS, vol. 115, No. 8, 2018, pp. 1690-1692.

Vapnik, "An Overview of Statistical Learning Theory", IEEE Transactions on Neural Networks, vol. 10, No. 5, 1999, pp. 988-999.

Cristianini et al., "An Introduction to Support Vector Machines and other kernal-based Learning Methods", Cambridge University Press, 2000, 13 pages.

Karatzoglou et al., "Suport Vector Machines in R", Journal of Statistical Software, vol. 15, No. 9, 2006, pp. 1-28.

Joyce, "Bayes' Theorem", The Stanford Encyclopedia of Philosophy, 2003, pp. 1-16.

Gutierrez et al., "Respiratory rate variability in sleeping adults without obstructive sleep apnea", Physiological Reports, vol. 4, No. 17, 2016, pp. 1-9.

Han et al, "Data Mining Concepts and Techniques", Third Edition, The Morgan Kaufmann Series in Data Management Systems, 2012, 740 pages.

LeCun et al., "Convolutional Networks for Images, Speech, and Time-Series", in Airbib (Ed.), The Handbook of Brain Theory and Neural Networks, 1995, 14 pages.

* cited by examiner

NEUROMODULATION AND OTHER THERAPIES TO TREAT A COMBINATION OF OBSTRUCTIVE SLEEP APNEA AND CENTRAL SLEEP APNEA

CROSS REFERENCE TO RELATED APPLICATION(S)

This application claims the benefit of U.S. Provisional Application Ser. No. 63/476,877, entitled "NEUROMODULATION AND OTHER THERAPIES TO TREAT A COMBINATION OF OBSTRUCTIVE SLEEP APNEA AND CENTRAL SLEEP APNEA" and filed on Dec. 22, 2022, which is expressly incorporated by reference herein in its entirety.

TECHNICAL FIELD

The present disclosure generally relates to systems and methods for treating both obstructive sleep apnea (OSA) and central sleep apnea (CSA) using an implantable pulse generator (IPG), and methods of treating medical conditions related thereto.

BACKGROUND

Sleep apnea is a type of sleep-related breathing disorder marked by abnormal reductions in breathing while a person is asleep. These disruptions reduce the quality of sleep and, if left untreated, can lead to potentially serious health consequences. Sleep apnea is a common disorder in the United States, but often goes undiagnosed because many sleepers are unaware of their nighttime symptoms. Sleep apnea exists in two major forms—obstructive sleep apnea (OSA) where the airway is physically blocked by a collapse of the tongue and/or soft palette and central sleep apnea (CSA) where the signal from the brain to the muscles that control breathing (i.e., diaphragm) is periodically blocked resulting in over breathing and under breathing.

OSA is a sleep disorder involving obstruction of the upper airway during sleep. The obstruction of the upper airway may be caused by the collapse of or increase in the resistance of the pharyngeal airway, often resulting from tongue obstruction. The obstruction of the upper airway may be caused by reduced genioglossus muscle activity during the deeper states of Non-Rapid Eye Movement (NREM) sleep. Obstruction of the upper airway may cause breathing to pause during sleep. Cessation of breathing may cause a decrease in the blood oxygen saturation level, which may eventually be corrected when the person wakes up and resumes breathing. The long-term effects of OSA include high blood pressure, heart failure, strokes, diabetes, headaches, and general daytime sleepiness and memory loss, among other symptoms.

OSA is extremely common, and may have a prevalence similar to diabetes or asthma. Over 100 million people worldwide suffer from OSA, with about 25% of those people being treated. Continuous Positive Airway Pressure (CPAP) is a conventional therapy for people who suffer from OSA. More than five million patients own a CPAP machine in North America, but many do not comply with use of these machines because they cover the mouth and nose and, hence, are cumbersome and uncomfortable.

CSA is a sleep disorder in which breathing repeatedly stops and starts during sleep. CSA may be caused by an underlying medical condition, recent ascent to high altitude, or narcotic use. Unlike OSA, in CSA, the problem is not a blocked airway. Instead, pauses in breathing occur because the brain and the muscles that control breathing do not function properly. As a result, a person with CSA repeatedly stops trying to breathe as they sleep. CSA may lead to complications including fatigue and cardiovascular problems. For instance, sudden drops in blood oxygen levels that occur during CSA may adversely affect heart health. If there is an underlying heart disease, these repeated multiple episodes of low blood oxygen (hypoxia or hypoxemia) worsen prognosis and increase the risk of abnormal heart rhythms. In addition, the long-term effects of CSA include a higher risk of stroke, obesity, diabetes, heart attack or heart failure, uneven heartbeat, high blood pressure, headaches, and general daytime sleepiness and memory loss, among other symptoms.

CSA is less common than OSA, but may still affect about 10% of people. A single central apnea event is a greater than or equal to 10-second pause in ventilation with no associated respiratory effort. CSA is present when a patient has greater than five central apneas per hour of sleep with associated symptoms of disrupted sleep.

Neuromodulation is a technology that acts directly upon nerves by altering nerve activity by delivering stimulation (electrical, mechanical, magnetic, ultrasonic, etc.) or pharmaceutical agents directly to a target area. Neurostimulation devices work by actively stimulating nerves to produce a natural biological response. Specifically, neurostimulation devices involve the application of stimulation (typically, but not necessarily electrical stimulation) to the brain, the spinal cord, central nerves, or peripheral nerves. Neurostimulators may be used to open the upper airway as a treatment for alleviating apneic events. Such therapy may involve stimulating the nerve fascicles of the hypoglossal nerve (HGN) that innervate the intrinsic and extrinsic muscles of the tongue in a manner that prevents retraction of the tongue which would otherwise close the upper airway during the inspiration period of the respiratory cycle. ImThera Medical, now part of LivaNova, is currently testing, in an Food and Drug Administration (FDA) clinical trial, a stimulator system that is used to stimulate the trunk of the hypoglossal nerve stimulation (HGN) with a nerve cuff electrode. The stimulation system does not provide a sensor or sensing, and therefore, the stimulation delivered to the HGN trunk is not synchronized to the respiratory cycle. Thus, the tongue and other muscles that are innervated by nerve fascicles of the HGN trunk are stimulated irrespective of the respiratory cycle—so called asynchronous stimulation.

While CPAP is the first line of defense against OSA and often used for CSA, each of OSA and CSA has an FDA-approved neuromodulation device that can be used to treat patients who are refractive to CPAP or cannot tolerate CPAP. For OSA, HGN stimulation can be used to move the tongue forward on inspiration and maintain airway patency, while, for CSA, the phrenic nerve (PN) can be used to pace the diaphragm.

In practice, most sleep apnea patients have some combination of OSA and CSA with roughly 80% having predominantly OSA and the other 20% predominantly having CSA. However, there is no implantable device that currently treats both modalities of sleep apnea. Instead, commercially available neuromodulation devices treat just one or the other.

BRIEF SUMMARY OF EXEMPLARY ASPECTS OF THE DISCLOSURE

Ideally, an implantable neuromodulation system should be able to treat both OSA and CSA. In addition, it may be desirable to perform treatment of OSA and CSA without detection and classification of an apneic event or hypopnea event. It may also be helpful to deliver stimulation therapy to one or more targets that can treat both OSA and CSA continuously throughout the duration of sleep, or when probabilistic indicators show that apnea is likely to occur in the near future. Stimulation can be synchronous with anticipated respiration or a respiration signal provided by a subject's body, or it may be asynchronous (e.g., that is not dependent on) to respiration. The system can also be used to monitor and/or stimulate targets (including those unrelated to OSA or CSA) to treat underlying conditions which are frequently comorbid with OSA or CSA either by using the same implantable pulse generator (IPG) or in concert with one or more additional IPGs and/or external stimulators. For instance, some of the underlying conditions associated with OSA or CSA may include heart failure, atrial fibrillation, stroke, kidney failure, hypertension, and diabetes.

Moreover, there is a need in the art for an implantable neuromodulation system that can treat both OSA and CSA using concurrent or alternating stimulation of the hypoglossal nerve (HGN) and phrenic nerve (PN), or other targets that are appropriate to alleviate or prevent either CSA or OSA. For instance, since most patients have some combination of OSA and CSA, there should be an implantable device that can simultaneously treat both sleeping disorders. In addition, OSA and CSA systems may require performing a detection step of detecting an apneic event and a classification step to classify the apneic event or hypopnea event as either OSA or CSA before delivering electrical stimulation to the subject. Both the detection and classification steps are computationally intensive and also introduce a probability for errors to occur. In addition, it is often too late to terminate the apneic event or hypopnea event, or series of events, by the time apnea is detected.

The present disclosure addresses these and other shortcomings by providing systems and methods that can stimulate both the HGN and PN (or other relevant targets) to treat OSA and CSA without detection and classification steps. Accordingly, the system may have the capability to stimulate additional targets to alleviate or treat comorbid indications (which may also, but not necessarily, alleviate sleep apnea). For instance, the system may also stimulate other targets related to a body organ such as the laryngeal nerve, or motor end points, and muscles such as the diaphragm and the heart to provide relief from OSA and/or CSA, and/or comorbid conditions. Some other targets related to a body organ may include carotid baroreceptors, and/or vagus nerve for heart failure or hypertension, the heart for atrial fibrillation, the stomach for gastric pacing, or the liver, pancreas, vagus nerve, gut, and/or carotid sinus for diabetes.

The following presents a simplified summary of several exemplary embodiments in order to provide a basic understanding of the inventions described herein. This summary is not intended as an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In a first general aspect, the disclosure provides a system for treatment of CSA and OSA in a subject, comprising: an IPG coupled to a first electrode on a first lead and a second electrode on a second lead, wherein the first electrode is configured to stimulate a HGN of the subject and the second electrode is configured to stimulate a PN of the subject; a controller comprising a processor and memory, communicatively linked to the IPG and configured to: command the first electrode to deliver a stimulation signal to stimulate the HGN to move a tongue of the subject forward and/or stiffen an airway of the subject for alleviating an obstruction caused by OSA, and command the second electrode to deliver an inspiration stimulation signal to stimulate the PN based on a duty cycle for treating CSA by driving a respiration pace for the subject. The first electrode delivers the stimulation signal to stimulate the HGN according to the respiration pace driven by the inspiration stimulation signal.

In some aspects, the controller may be further configured to: provide a signal for when to start and stop commanding the first electrode. In some aspects, the controller is further configured to command the first electrode to deliver the stimulation signal to the HGN preferably 0 to 500 milliseconds before commanding the second electrode to deliver the inspiration stimulation signal to a diaphragm via the PN or motor point to produce inspiration. In some aspects, both the first electrode is commanded to deliver the stimulation to the HGN and the second electrode is commanded to deliver the inspiration stimulation signal to the PN to treat CSA without detection or classification of an apneic event or hypopnea event.

In some aspects, the controller may be further configured to detect whether a sleep disordered breathing (SDB) event is likely to occur in the subject based on sensor data obtained from one or more sensors. The second electrode being commanded to deliver the inspiration stimulation signal to the PN based on a determination that a SDB is likely to occur in the subject based on the sensor data.

In some aspects, the controller may be further configured to: generate (or store in a memory) a probabilistic function based on a data source that includes predictive data indicative of apnea and hypopnea events determined based on a sleep study. The probabilistic function may be generated or tuned based on machine learning algorithms. The likelihood of impending SDB events may be determined based on the probabilistic function, with or without additional inputs from sensors.

In some aspects, the determination that SDB is likely to occur may be further determined using probabilistic function and sensor data corresponding to one or more of blood oxygen level, blood pressure, heart rate, heart rate variability, electrocardiogram (ECG) data, electroencephalogram (EEG) data, electromyography (EMG) results, impedance, cardiothoracic impedance, sleep state, accelerometer data, or auscultation, and combinations thereof.

In a second general aspect, a method for treatment of CSA and OSA in a subject, may comprise: delivering, via a first electrode that is connected by a lead to the IPG, a stimulation signal to deliver stimulation to HGN of the subject to move a tongue of the subject forward and/or stiffen an airway of the subject for alleviating an obstruction caused by OSA; and delivering, via a second electrode that is connected by a lead to the IPG, an inspiration stimulation signal to deliver stimulation to a PN of the subject based on a duty cycle for treating CSA by driving a respiration pace to pace breathing for the subject. The first electrode being commanded to deliver the stimulation signal to stimulate the HGN according to the respiration pace driven by the inspiration stimulation signal.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

Figure 1:
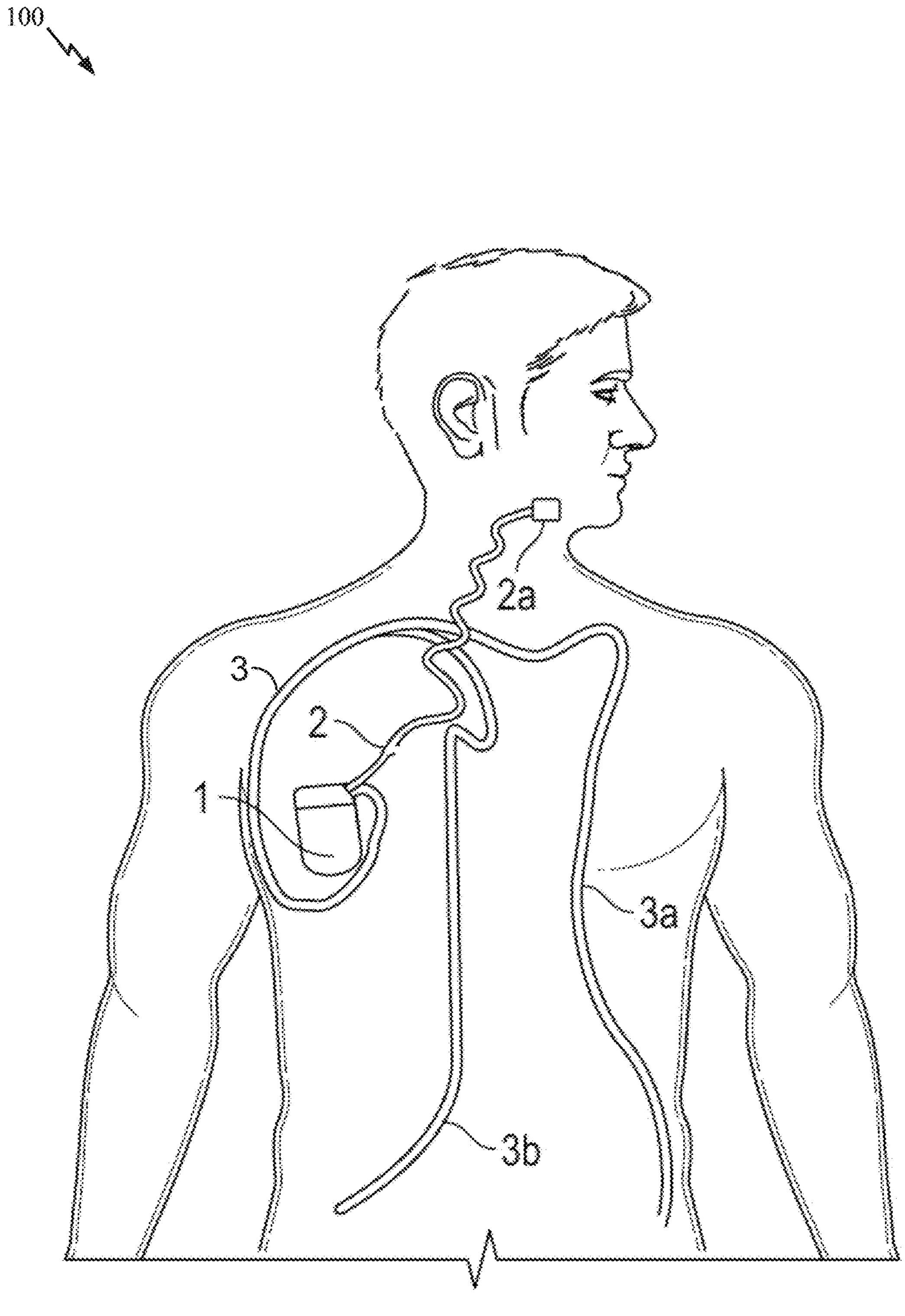
FIG. 1 is a diagram illustrating an exemplary embodiment of an implantable stimulation system for treating both OSA and CSA for a human subject. In this example, the system includes at least an IPG coupled to HGN lead and to PN lead. Both the HGN and PN leads are connected to the "header" portion of the housing of the IPG, which header has ports for accepting insertion of the proximal ends of the HGN and PN leads.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

As noted above, the present disclosure is generally directed to systems and methods for treating both OSA and CSA using concurrent or alternating stimulation of the HGN and PN, and methods of treating medical conditions related thereto. The implantable stimulation system does not require any detection and classification of an apneic event or hypopnea event. Instead, respiration and apnea/hypopnea sensing is not required because the implantable stimulation system is configured to deliver stimulation therapy to both targets that can treat both OSA and CSA by stimulating the PN to drive inspiration to treat CSA by forcing a breathing pace for the subject and then, stimulating the HGN to alleviate OSA according to the breathing pace. Furthermore, the stimulation system may stimulate both targets continuously (on a duty cycle) throughout the duration of sleep or turn on stimulation when it is determined that sleep disordered breathing is impending to save power consumption for the device. Turning on the stimulation only when necessary may also help the subject be more comfortable since stimulation is not occurring all the time.

In addition, for the systems that treat either OSA or CSA, the related systems must initially detect an apneic event or hypopnea event using sensor data measurements, classify the detected apneic event or hypopnea event as either OSA or CSA, respectively, and then deliver electrical stimulation to an appropriate target based on the detection and classification. In these systems, the detection and classification step introduces extra steps which require more sensing, energy and processing power. Moreover, such systems may also make mistakes based on a wrong classification of the apneic event or hypopnea event, or inaccurate detection of events.

Furthermore, although most patients with sleep apnea exhibit both OSA and CSA, currently marketed systems treat only either OSA or CSA, but not both. Each of OSA and CSA has an FDA approved neuromodulation device that can be used to treat patients who are refractive to CPAP or cannot tolerate CPAP. For instance, for OSA, HGN stimulation can be used to move the tongue forward on inspiration and maintain airway patency and, for CSA, the PN stimulation can be used to pace the diaphragm and drive breathing.

A company, Inspire Medical Systems, Inc., offers a stimulation system with a respiration sensor, and, therefore, attempts to time the onset of stimulation to a breathing cycle. The Inspire system, which has been FDA approved for sale in the United States since April 2010, uses a simple, bipolar electrode (two electrode contacts only) within a nerve cuff electrode and implants the electrode at the branch of the HGN that is responsible for protruding the tongue. A simple, two-electrode contact or three-electrode contact cuff electrode can be used at the branch nerve, unlike the HGN trunk, because at the distal branch location, the nerve fascicles generally innervate the specific tongue protrusion muscle and not other muscles. A pressure sensor is connected to the neurostimulator of the Inspire system by a lead to attempt to determine when a subject is about to inspire. The Inspire system then uses the measured respiration to time stimulation just in advance of inspiration (e.g., 200-300 ms before respiration). As will be described in more detail below, it is difficult to consistently and reliably detect respiration on every inspiration and expiration in a subject. In addition, the fact that the pressure sensor has a lead connected to the stimulator necessitates some additional surgery, because the sensor lead is another appendage that must be implanted.

Another company Respicardia, now part of ZOLL Medical Corporation, offers a stimulation system named the remedē system to treat CSA alone. The remedē system, approved by the FDA since 2017, also uses a pressure sensor to detect when the breathing effort of a subject is absent by monitoring their lungs. However, similar to the Inspire system, the remedē system relies on using sensors to determine when the subject is about to inspire and it is difficult to accurately detect respiration from the subject. As will be further described below, the present disclosure does not rely on using any respiration sensors to determine the timing of stimulation.

In contrast, the implantable stimulation system described herein simplifies and improves on existing designs by treating both OSA and CSA using stimulation of the HGN for OSA and PN for CSA. A system according to this disclosure may deliver stimulation therapy to both the HGN and PN continuously (although on a duty cycle) throughout the duration of sleep for a subject or when probabilistic indicators predict that apnea or hypopnea is likely to occur without requiring a detection and classification of an SDB event (e.g., whether the apneic event or hypopnea event is OSA or CSA). Systems according to this disclosure pace respiration by stimulating the phrenic nerve alleviating CSA, and stimulating the HGN for relieving OSA based on the paced respiration driven by the system. Thus, instead of measuring respiration to determine when to stimulate an OSA target, the system may provide a stimulation to a diaphragm through the PN to drive breathing according to a respiration pace and then use the timing of that stimulus to determine when to stimulate the HGN. This removes a challenge in related systems that must rely on determining or measuring respiration for stimulating targets.

Systems according to the disclosure may also be configured to stimulate additional targets related to a body organ such as the vagus nerve, laryngeal nerve, motor end points (e.g., nerve end points innervating muscles), diaphragm, and the heart to provide relief from comorbidities associated with OSA and/or CSA. For instance, such systems may also monitor and/or stimulate other targets to treat underlying conditions which are frequently comorbid with CSA or OSA. This may in turn lead to alleviating or treating other targets and comorbid indications such as carotid baroreceptors, and/or vagus nerve for heart failure or hypertension, the heart for atrial fibrillation, and multiple potential targets for diabetes (e.g., liver, pancreas, vagus nerve, or carotid sinus), or the stomach for gastric pacing for obesity.

FIG. 1 is a diagram illustrating an embodiment of a system 100 for treating OSA and CSA for a human subject. In this example, the system 100 comprises an IPG 1 integrated into a housing of the system 100 with one or more stimulating circuits within the IPG. Each stimulating circuit may be connectable to a different lead, and each circuit may have a plurality of stimulating channels connecting to different electrode contacts on a stimulating lead.

As shown in FIG. 1, an IPG 1 connects to one or more leads 2 and 3 to effect stimulation of at least two targets (e.g., the HGN and PN). In some aspects, the system 100 may consist of one stimulation lead going to multiple targets or multiple stimulation leads. In some aspects, the system 100 may consist of a first IPG 1 connected to a first stimulation lead for stimulating one target site (e.g., the HGN) and a second IPG (not shown in FIG. 1) connected to second stimulation lead for stimulating a second site (e.g., the PN).

Specifically, in system 100, the IPG 1 is coupled to an HGN lead 2 and CSA lead 3. The HGN lead 2 terminates with a stimulating cuff electrode 2*a*. The stimulating cuff electrodes 2*a* deliver stimulation to a HGN which innervates one or more upper airway muscles of the subject. For instance, the HGN lead 2 terminates in a stimulating cuff electrode 2*a* that may be located at either the distal or proximal end of the HGN. The CSA lead 3 bifurcates to a stimulating lead 3*a* and an optional sensing lead 3*b*. The stimulating lead 3*a* also extend from the IPG 1 to deliver stimulation to one or more locations of the PN (e.g., the left pericardiophrenic vein or the right brachiocephalic vein) of the subject. For instance, the CSA lead 3 bifurcates into the stimulating lead 3*a* in the pericardiophrenic vein adjacent to PN and an optional sensing 3*b* lead in the azygos vein.

The system 100 is configured to pace respiration of the subject by delivering stimulation to the PN of the subject to drive an inspiration through the CSA leads 3*a*. In some aspects, the pacing signal is used to synchronize HGN stimulation in order to move a subject's tongue forward and to increase airway patency prior to inspiration to relieve OSA. In this situation, the system 100 may provide a signal or time point for when stimulation to the HGN would start and stop based on the respiration pace. This embodiment is helpful because the system 100 may be configured to stimulate the HGN based on an "artificial" respiration pace driven by stimulating the PN. Thus, this embodiment does not have to rely on measuring respiration, or detecting and classifying SDB events to determine when to stimulate an OSA or CSA target.

In some aspects, potential sensors used to determine whether SDB is likely to occur may include a heart rate monitor, an electrocardiogram (EKG), a blood pressure sensor, a blood oxygen level sensor (including photoplethysmography), an electromyography (EMG) sensor, and/or a muscle sympathetic nerve activity (MSNA) sensor. Sensors located in the body are typically more accurate than those located outside the body, and so, to the extent that any of these measured parameters are indicative of sleep stage and/or quality, the implanted device has the ability to determine more information, and more accurate information than an external device. However, in some aspects, the sensors (e.g., microphone) may be located outside the body.

In some aspects, optional sensors may also be used to assist in determining when SDB is likely to occur using an optional sensing lead 3*b* in the azygos vein. For instance, the system 100 may be further equipped with one or more sensors with sensing capabilities to determine when SDB is imminent or likely to occur using sensor measurement data corresponding to one or more of blood oxygen level, blood pressure, heart rate, heart rate variability, ECG, EEG, EMG, impedance, cardiothoracic impedance, sleep state, accelerometer, auscultation, respiratory effort, or the like. As a non-limiting example, the potential sensors may detect events such as atrial fibrillation, acute heart failure, reduced blood oxygen levels, elevated glucose levels, or any of a number of other states, and then sound an alarm, record the event, and/or trigger the consequent delivery of bioelectronic therapy, and/or medication or compound delivered orally, by injection, by inhalation, through a pump, or produced endogenously in the body. Said compound includes one or more of oxygen, insulin, glucose, heart medications, anti-coagulants, pain medications, and many other possibilities.

Since OSA is often the result of obesity and/or substance abuse and may result in hypertension, diabetes, liver damage, and heart problems, and CSA is often caused by heart failure, atrial fibrillation, stroke, kidney disease, and/or diabetes, the system may also deliver stimulation to other targets (e.g., vagus nerve, carotid sinus, carotid baroreceptors, liver, stomach, pancreas, etc.) to treat these conditions and/or monitor the status of these conditions (i.e. detect the occurrence of atrial fibrillation, or monitor levels of glucose or hemoglobin A1C), and to trigger an alarm or alternative medical intervention accordingly. In some aspects, the sensing of biomarkers for the given comorbidity could be on the lead, on the IPG 1, in the IPG 1, elsewhere in the body or outside the body with the ability to communicate with the system.

In some aspects, the system 100 may have the ability to monitor one or more of the common comorbidities associated with sleep apnea, OSA, and/or CSA. As such, the system 100 may have a further capability to stimulate additional targets related to body organs to alleviate or treat comorbid indications which may also, but not necessarily, alleviate sleep apnea. In some aspects, a lead or electrode (not shown in FIG. 1) may extend to other potential targets such as carotid sinus, carotid baroreceptors, heart, liver, other branches of the vagus nerve, stomach, liver, or pancreas. As a non-limiting example, the system 100 may stimulate the carotid baroreceptors and/or vagus nerve for relieving and/or treating heart failure, the heart for relieving and/or treating atrial fibrillation, multiple potential targets (e.g., liver, pancreas, vagus nerve, carotid sinus, or the like) for relieving and/or treating diabetes, and a stomach for relieving and/or treating gastric pacing to treat obesity.

The resulting system is potentially a complex system of multiple stimulation targets, and sensors to determine when SDB is likely, and other sensors to monitor biological markers of disease. Such a system lends itself to a complex control algorithm to deliver optimal therapy, and in one embodiment this control could be the result of machine learning (or artificial intelligence).

Figure 2:
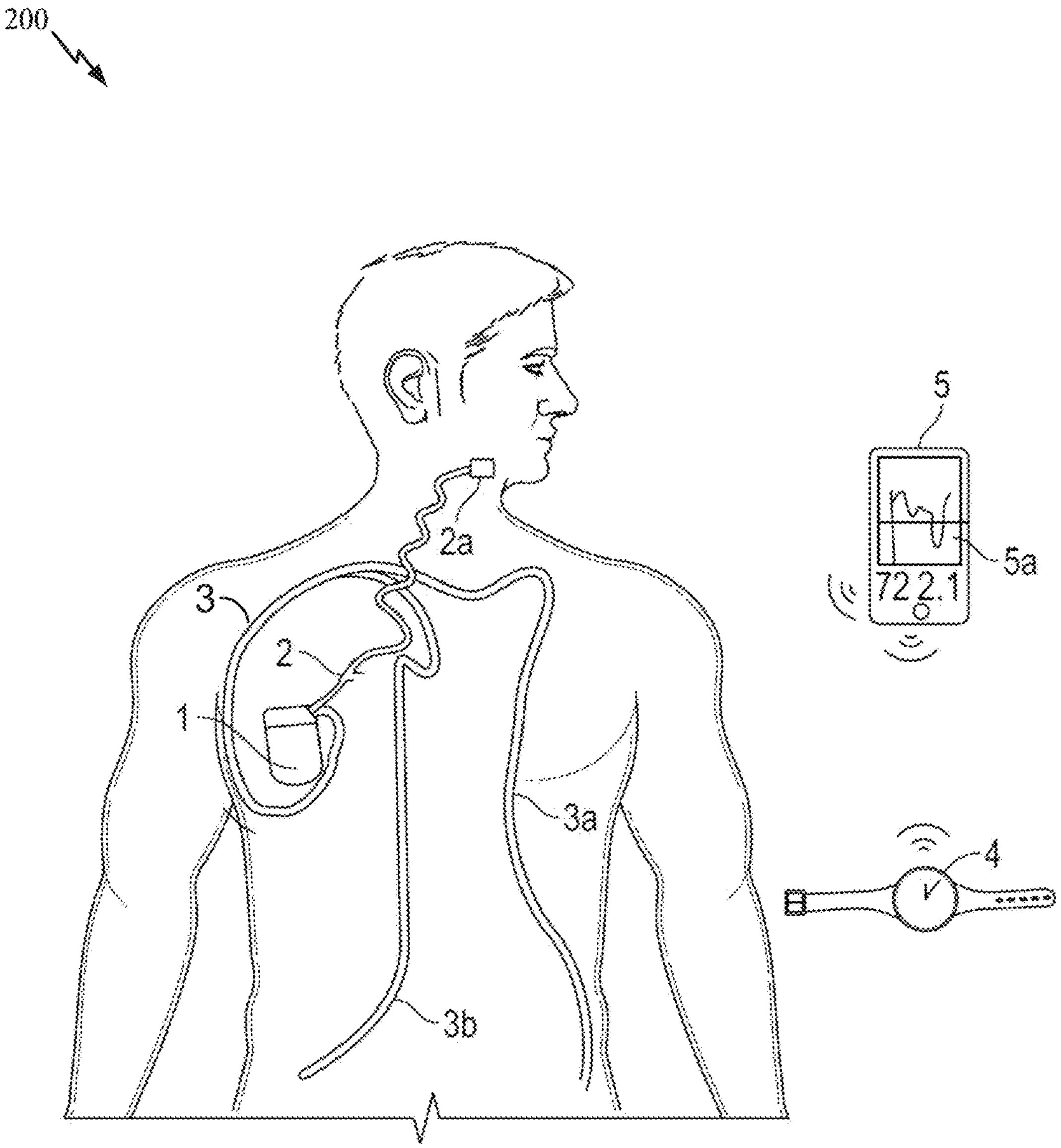
FIG. 2 is a diagram illustrating another exemplary embodiment of an implantable stimulation system for treating both OSA and CSA for a human subject. In this example, the system comprises an external system, as well as an implanted sensor typically mounted on a distal part of the lead. The proximal part of the sensor lead is connected to the housing of an implanted OSA IPG or stimulator. Optional external components of a system according to the disclosure are also illustrated.

FIG. 2 is a diagram illustrating another exemplary embodiment of an implantable stimulation system 200 for treating both OSA and CSA for a human subject. Optional external components of a system according to the disclosure are also illustrated. In this example, the system 200 comprises an external system controller 5, as well as an implanted IPG 1 with sensing capability integrated into the housing of an implanted OSA stimulation system. In this example, the system 200 comprises an external sensor 4 (e.g., a wrist worn sensor), as well as an implanted controller and implanted IPG 1 integrated into the housing of an implanted stimulation system 200. An external system controller 5 and optional cloud-based components of a system according to the disclosure are also illustrated.

The IPG system controller inside the IPG 1 can be wirelessly communicatively linked to the external system controller 5. As described herein, the external system controller 5 is configured to receive sensor data measurement, determine if SDB is occurring or likely to occur, determine if co-morbidities are being exacerbated, and/or provide appropriate control signals to the IPG 1. The external system controller 5 may be included in any one of a smart phone, a tablet, or any other similar device.

The external system controller 5 may also include a user application 5*a* capable of displaying sensor data, IPG data, therapy status, event detection, alerts, recording, and transmitting data for remote review or action. This allows the external system controller 5 to cause an output of an alert that may be audible, tactile, and/or visual on an external device or the external sensor 4 (e.g., the wrist-worn sensor). In some aspects, the external system controller 5 is capable of sounding audible alarms, recording data for real time and/or subsequent transmission to a patient, health provider, and/or a data aggregator, including wireless cloud based transmission to a remote location.

In this example, the implantable stimulation system 200 comprises two sensors. The external sensor 4 may be a wrist-worn sensor integrated into a smart watch or fitness tracker (e.g., a heart rate sensor or photoplethysmography sensor). For instance, the external sensor 4 may have sensors such as photoplethysmography (PPG), ECG, inertia measurement unit (IMU), gyroscope, microphone, and/or infrared capable of detecting glucose levels, heart rate, blood pressure, apnea-hypopnea index (AHI), snoring, sleep stage detection, blood oxygen levels ($SpO_2$), and/or heart rate variability (HRV). Although FIG. 2 shows the external sensor 4 as a wrist-worn watch, the system 200 may include any type of external sensor such as a ring, a chest-worn sensor, a head-worn sensor, a sensor not located on the body, or the like with sensing capabilities. The implanted IPG sensor 1 may be an IMU, gyroscope, ECG electrode(s), pressure sensor, and/or microphone for respiration, heart rate, snoring, or AHI detection. In this case, the implanted controller is capable of wireless communication with the external sensor 4 and with an external controller 5. The external system controller 5 may be a dedicated controller with a text-based or graphical user interface, or software executed on a smart phone, tablet, computer, or other multi-purpose electronic device. The implanted controller and/or the external system controller 5 may also be configured to communicate with one or more local, remote, or cloud-based servers. For example, in this case the external system controller 5 may be capable of communicating with a remote server via intermediary cloud-based infrastructure.

In some aspects, the external system controller 5 may be configured to execute a user application 5*a* configured to communicate with a clinical application via an intervening cloud infrastructure, allowing a remote clinician to interact with the external controller or the implanted controller. This configuration may allow for a clinician to view a subject's data, including sleep quality metrics, sensor data, detected events, implant health, alarms, and to view and/or modify one or more settings of the stimulation system. For example, the clinician may be able to edit a stimulation profile or individual parameters stored on the external controller 5, which may, in turn, be transmitted to the implanted controller in order to modify the treatment regimen or stimulation parameters applied by the stimulation system 200.

In some aspects, the system 200 may be configured to deploy a machine learning algorithm to coordinate sensing, monitoring, and stimulation. For instance, the implantable stimulation system 200 may be configured to generate a probabilistic function based on a data source that includes predictive data indicative of apnea and hypopnea events determined based on a sleep study. The probabilistic function may be generated or tuned based on a classifier comprising a machine learning algorithms and/or deep learning algorithms and to determine that SDB is likely to occur in the subject based on the probabilistic function. In some aspects, the classifier comprises one or more of: AdaBoost, Artificial Neural Network (ANN) learning algorithm, Bayesian belief networks, Bayesian classifiers, Bayesian neural networks, Boosted trees, case-based reasoning, classification trees, Convolutional Neural Networks, decisions trees, Deep Learning, elastic nets, Fully Convolutional Networks (FCN), genetic algorithms, gradient boosting trees, k-nearest neighbor classifiers, LASSO, Linear Classifiers, naive Bayes classifiers, neural nets, penalized logistic regression, Random Forests, ridge regression, support vector machines, or an ensemble thereof.

Determination of probabilistic functions will require an objective data source that reflects measurements of apnea and hypopnea events in order to inform a training algorithm for machine learning. This data could be collected during a Polysomnography (PSG) sleep study that determines when these events occur and also measures several of the predictive variables described above (i.e. oxygen levels, blood pressure, heart rate, respiration rate) or be based on intra-patient data collected over time, or inter-patient data collected over time suggesting probabilities that cover a larger population. For predictive variables not typically collected during a PSG study, additional sensors may be required at the time the PSG is conducted, and the sensor measurement outputs may need to be synchronized to the PSG data collection device. While many PSG studies are conducted in sleep labs, there are many options to conduct these studies at home, as well. Once a comprehensive data set of apneic and hypopnea events along with predictive input data has been collected for a patient, there are several data analysis algorithms that could be used to develop predictive capabilities for the system. These could be a simple a linear regression models conducted with single explanatory variables, to multiple regression, and even non-linear regression. However, since the number of possible explanatory variables is high, it may be possible to develop better classifiers or predictive algorithms using machine learning, and specifically machine learning algorithms as support vector machine(s), AdaBoost classifier(s), penalized logistic regression, elastic nets, regression tree system(s), gradient tree boosting system(s), naive Bayes classifier(s), neural nets, Bayesian neural nets, k-nearest neighbor classifier(s), deep learning systems, and random forest classifiers.

Classifiers

The term "classifier," as used herein, refers broadly to a machine learning algorithm such as support vector machine(s), AdaBoost classifier(s), penalized logistic regression, elastic nets, regression tree system(s), gradient tree boosting system(s), naive Bayes classifier(s), neural nets, Bayesian neural nets, k-nearest neighbor classifier(s), deep learning systems, and random forest classifiers. The systems and methods described may use any of these classifiers, or combinations thereof.

A "Classification and Regression Trees (CART)," as used herein, refers broadly to a method to create decision trees based on recursively partitioning a data space so as to optimize one or more metrics, e.g., model performance.

The classification systems used herein may include computer executable software, firmware, hardware, or combinations thereof. For example, the classification systems may include reference to a processor and supporting data storage. Further, the classification systems may be implemented across multiple devices or other components local or remote to one another. The classification systems may be implemented in a centralized system, or as a distributed system for additional scalability. Moreover, any reference to software may include non-transitory computer readable media that when executed on a computer, causes the computer to perform one or more steps.

There are many potential classifiers that can be used by the systems and methods described herein. Machine and deep learning classifiers include but are not limited to AdaBoost, Artificial Neural Network (ANN) learning algorithm, Bayesian belief networks, Bayesian classifiers, Bayesian neural networks, Boosted trees, case-based reasoning, classification trees, Convolutional Neural Networks, decisions trees, Deep Learning, elastic nets, Fully Convolutional Networks (FCN), genetic algorithms, gradient boosting trees, k-nearest neighbor classifiers, LASSO, Linear Classifiers, naive Bayes classifiers, neural nets, penalized logistic regression, Random Forests, ridge regression, support vector machines, or an ensemble thereof. See, e.g., Han & Kamber (2006) Chapter 6, Data Mining, Concepts and Techniques, 2nd Ed. Elsevier: Amsterdam. As described herein, any classifier or combination of classifiers (e.g., an ensemble) may be used by the present systems.

Deep Learning Algorithms

In some aspects, the classifier is a deep learning algorithm. Machine learning is a subset of artificial intelligence that uses a machine's ability to take a set of data and learn about the information it is processing by changing the algorithm as data is being processed. Deep learning is a subset of machine learning that utilizes artificial neural networks inspired by the workings on the human brain. For example, the deep learning architecture may be multilayer perceptron neural network (MLPNN), backpropagation, Convolutional Neural Network (CNN), Recurrent Neural Network (RNN), Long Short-Term Memory (LSTM), Generative Adversarial Network (GAN), Restricted Boltzmann Machine (RBM), Deep Belief Network (DBN), or an ensemble thereof.

Classification Trees

A classification tree is an easily interpretable classifier with built in feature selection. A classification tree recursively splits the data space in such a way so as to maximize the proportion of observations from one class in each subspace.

The process of recursively splitting the data space creates a binary tree with a condition that is tested at each vertex. A new observation is classified by following the branches of the tree until a leaf is reached. At each leaf, a probability is assigned to the observation that it belongs to a given class. The class with the highest probability is the one to which the new observation is classified. Classification trees are essentially a decision tree whose attributes are framed in the language of statistics. They are highly flexible but very noisy (the variance of the error is large compared to other methods).

Tools for implementing classification tree are available, by way of non-limiting example, for the statistical software computing language and environment, R. For example, the R package "tree," version 1.0-28, includes tools for creating, processing and utilizing classification trees. Examples of Classification Trees include but are not limited to Random Forest. See also Kamiński et al. (2017) "A framework for sensitivity analysis of decision trees." *Central European Journal of Operations Research.* 26(1): 135-159; Karimi & Hamilton (2011) "Generation and Interpretation of Temporal Decision Rules", *International Journal of Computer Information Systems and Industrial Management Applications*, Volume 3, the content of which is incorporated by reference in its entirety.

Random Forest Classifiers

Classification trees are typically noisy. Random forests attempt to reduce this noise by taking the average of many trees. The result is a classifier whose error has reduced variance compared to a classification tree. Methods of building a Random Forest classifier, including software, are known in the art. Prinzie & Poel (2007) "Random Multiclass Classification: Generalizing Random Forests to Random MNL and Random NB." *Database and Expert Systems Applications. Lecture Notes in Computer Science.* 4653; Denisko & Hoffman (2018) "Classification and interaction in random forests." *PNAS* 115(8): 1690-1692, the contents of which are incorporated by reference in its entirety.

To classify a new observation using the random forest, classify the new observation using each classification tree in the random forest. The class to which the new observation is classified most often amongst the classification trees is the class to which the random forest classifies the new observation. Random forests reduce many of the problems found in classification trees but at the tradeoff of interpretability.

Tools for implementing random forests as discussed herein are available, by way of non-limiting example, for the statistical software computing language and environment, R. For example, the R package "random Forest," version 4.6-2, includes tools for creating, processing and utilizing random forests.

AdaBoost (Adaptive Boosting)

AdaBoost provides a way to classify each of n subjects into two or more categories based on one k-dimensional vector (called a k-tuple) of measurements per subject. AdaBoost takes a series of "weak" classifiers that have poor, though better than random, predictive performance and combines them to create a superior classifier. The weak classifiers that AdaBoost uses are classification and regression trees (CARTs). CARTs recursively partition the dataspace into regions in which all new observations that lie within that region are assigned a certain category label. AdaBoost builds a series of CARTs based on weighted versions of the dataset whose weights depend on the performance of the classifier at the previous iteration. See Han & Kamber (2006) *Data Mining, Concepts and Techniques,* 2nd Ed. Elsevier: Amsterdam, the content of which is incorporated by reference in its entirety. AdaBoost technically works only when there are two categories to which the observation can belong. For g>2 categories, (g/2) models must be created that classify observations as belonging to a group or not. The results from these models can then be combined to predict the group membership of the particular observation. Predictive performance in this context is defined as the proportion of observations misclassified.

Convolutional Neural Network

Convolutional Neural Networks (CNNs or ConvNets) are a class of deep, feed-forward artificial neural networks, most commonly applied to analyzing visual imagery. CNNs use a variation of multi-layer perceptrons designed to require minimal preprocessing. They are also known as shift invariant or space invariant artificial neural networks (SIANN), based on their shared-weights architecture and translation invariance characteristics. Convolutional networks were inspired by biological processes in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field. CNNs use relatively little pre-processing compared to other image classification algorithms This means that the network learns the filters that in traditional algorithms were hand-engineered. This independence from prior knowledge and human effort in feature design is a major advantage. LeCun and Bengio (1995) "Convolutional networks for images, speech, and time-series," in Arbib (Ed.), The Handbook of Brain Theory and Neural Networks, MIT Press, the content of which is incorporated by reference in its entirety. Fully convolutional indicates that the neural network is composed of convolutional layers without any fully-connected layers or MLP usually found at the end of the network. Convolutional Neural Network is an example of deep learning.

Support Vector Machines

Support vector machines (SVMs) are recognized in the art. In general, SVMs provide a model for use in classifying each of n subjects to two or more categories based on one k-dimensional vector (called a k-tuple) per subject. An SVM first transforms the k-tuples using a kernel function into a space of equal or higher dimension. The kernel function projects the data into a space where the categories can be better separated using hyperplanes than would be possible in the original data space. To determine the hyperplanes with which to discriminate between categories, a set of support vectors, which lie closest to the boundary between the disease categories, may be chosen. A hyperplane is then selected by known SVM techniques such that the distance between the support vectors and the hyperplane is maximal within the bounds of a cost function that penalizes incorrect predictions. This hyperplane is the one which optimally separates the data in terms of prediction. Vapnik (1998) *Statistical Learning Theory*; Vapnik "An overview of statistical learning theory" *IEEE Transactions on Neural Networks* 10(5): 988-999 (1999) the content of which is incorporated by reference in its entirety. Any new observation is then classified as belonging to any one of the categories of interest, based where the observation lies in relation to the hyperplane. When more than two categories are considered, the process is carried out pairwise for all of the categories and those results combined to create a rule to discriminate between all the categories. See Cristianini, N., & Shawe- Taylor, J. (2000). *An Introduction to Support Vector Machines and Other Kernel-based Learning Methods*. Cambridge: Cambridge University Press provides some notation for support vector machines, as well as an overview of the method by which they discriminate between observations from multiple groups.

In an exemplary embodiment, a kernel function known as the Gaussian Radial Basis Function (RBF) is used. Vapnik, 1998. The RBF may be used when no a priori knowledge is available with which to choose from a number of other defined kernel functions such as the polynomial or sigmoid kernels. See Han et al. *Data Mining: Concepts and Techniques*, Morgan Kaufman 3rd Ed. (2012). The RBF projects the original space into a new space of infinite dimension. A discussion of this subject and its implementation in the R statistical language can be found in Karatzoglou et al. “Support Vector Machines in R,” *Journal of Statistical Software* 15(9) (2006), the content of which is incorporated by reference in its entirety. All SVM statistical computations described herein were performed using the statistical software programming language and environment R 2.10.0. SVMs were fitted using the ksvm( ) function in the kernlab package. Other suitable kernel functions include, but are not limited to, linear kernels, radial basis kernels, polynomial kernels, uniform kernels, triangle kernels, Epanechnikov kernels, quartic (biweight) kernels, tricube (triweight) kernels, and cosine kernels. Support vector machines are one out of many possible classifiers that could be used on the data. By way of non-limiting example, and as discussed below, other methods such as naive Bayes classifiers, classification trees, k-nearest neighbor classifiers, etc. may be used on the same data used to train and verify the support vector machine.

Naïve Bayes Classifier

The set of Bayes Classifiers are a set of classifiers based on Bayes' Theorem. See, e.g., Joyce (2003), Zalta, Edward N. (ed.), “Bayes' Theorem”, *The Stanford Encyclopedia of Philosophy* (Spring 2019 Ed.), Metaphysics Research Lab, Stanford University, the content of which is incorporated by reference in its entirety.

Classifiers of this type seek to find the probability that an observation belongs to a class given the data for that observation. The class with the highest probability is the one to which each new observation is assigned. Theoretically, Bayes classifiers have the lowest error rates amongst the set of classifiers. In practice, this does not always occur due to violations of the assumptions made about the data when applying a Bayes classifier.

The naïve Bayes classifier is one example of a Bayes classifier. It simplifies the calculations of the probabilities used in classification by making the assumption that each class is independent of the other classes given the data. Naïve Bayes classifiers are used in many prominent anti-spam filters due to the ease of implantation and speed of classification but have the drawback that the assumptions required are rarely met in practice. Tools for implementing naive Bayes classifiers as discussed herein are available for the statistical software computing language and environment, R. For example, the R package “e1071,” version 1.5-25, includes tools for creating, processing and utilizing naive Bayes classifiers.

Neural Networks

One way to think of a neural network is as a weighted directed graph where the edges and their weights represent the influence each vertex has on the others to which it is connected. There are two parts to a neural network: the input layer (formed by the data) and the output layer (the values, in this case classes, to be predicted). Between the input layer and the output layer is a network of hidden vertices. There may be, depending on the way the neural network is designed, several vertices between the input layer and the output layer.

Neural networks are widely used in artificial intelligence and data mining but there is the danger that the models the neural nets produce will over fit the data (i.e., the model will fit the current data very well but will not fit future data well). Tools for implementing neural nets as discussed herein are available for the statistical software computing language and environment, R. For example, the R package “e1071,” version 1.5-25, includes tools for creating, processing and utilizing neural nets.

k-Nearest Neighbor Classifiers (KNN)

The nearest neighbor classifiers are a subset of memory-based classifiers. These are classifiers that have to “remember” what is in the training set in order to classify a new observation. Nearest neighbor classifiers do not require a model to be fit.

To create a k-nearest neighbor (knn) classifier, the following steps are taken:

1. Calculate the distance from the observation to be classified to each observation in the training set. The distance can be calculated using any valid metric, though Euclidian and Mahalanobis distances are often used. The Mahalanobis distance is a metric that takes into account the covariance between variables in the observations.
2. Count the number of observations amongst the k nearest observations that belong to each group.
3. The group that has the highest count is the group to which the new observation is assigned.

Nearest neighbor algorithms have problems dealing with categorical data due to the requirement that a distance be calculated between two points but that can be overcome by defining a distance arbitrarily between any two groups. This class of algorithm is also sensitive to changes in scale and metric. With these issues in mind, nearest neighbor algorithms can be very powerful, especially in large data sets. Tools for implementing k-nearest neighbor classifiers as discussed herein are available for the statistical software computing language and environment, R. For example, the R package “e1071,” version 1.5-25, includes tools for creating, processing and utilizing k-nearest neighbor classifiers.

Training Data

In another aspect, methods described herein include training of about 75%, about 80%, about 85%, about 90%, or about 95% of the data in the library or database and testing the remaining percentage for a total of 100% data. In an aspect, from about 70% to about 90% of the data is trained and the remainder of about 10% to about 30% of the data is tested, from about 80% to about 95% of the data is trained and the remainder of about 5% to about 20% of the data is tested, or from about 90% of the data is trained and the remainder of about 10% of the data is tested.

In some aspects, the database or library contains data from the analysis of over about 25, about 60, over about 125, over about 250, over about 500, or over about 1000 human subjects (collected using systems according to the disclosure, PSG studies, etc.). In some aspects, the data may comprise data from healthy subjects and/or from those known to have OSA or CSA.

The training data may comprise, e.g., data relating to any of the parameters described herein, including sensor data, biomarker data, environmental data, or any combinations thereof.

Methods of Classification

The disclosure provides for methods of classifying data (e.g., sensor data and/or biomarker data) obtained from an individual in order to determine the individual's sleep stage and to generate a sleep quality score. In some aspects, these methods involve preparing or obtaining training data, as well as evaluating test data obtained from an individual (as compared to the training data), using one of the classification systems including at least one classifier as described above. Preferred classification systems use classifiers such as, but not limited to, support vector machines (SVM), AdaBoost, penalized logistic regression, naive Bayes classifiers, classification trees, k-nearest neighbor classifiers, Deep Learning classifiers, neural nets, random forests, Fully Convolutional Networks (FCN), Convolutional Neural Networks (CNN), and/or an ensemble thereof. Deep Learning classifiers are a more preferred classification system. The classification system may be configured, e.g., to output a determination as to a subject's sleep stage or a sleep quality score, based on sensor data, biomarker data, or combinations thereof.

As noted above, in some aspects a classifier may comprise an ensemble of multiple classifiers. For example, an ensemble method may include SVM, AdaBoost, penalized logistic regression, naive Bayes classifiers, classification trees, k-nearest neighbor classifiers, neural nets, FCN, CNN, Random Forests, deep learning, or any ensemble thereof, in order to make any of the determinations described herein.

An exemplary method for classifying SDB may comprise the steps of: (a) accessing an electronically stored set of training data vectors, each training data vector or k-tuple representing an individual human subject and comprising sensor data and/or biometric data for the respective human subject for each replicate, the training data vector further comprising a classification with respect to a sleep stage and/or quality characterization of each respective human subject; (b) training an electronic representation of a classifier or an ensemble of classifiers as described herein using the electronically stored set of training data vectors; (c) receiving test data comprising a plurality of sensor data and/or biometric data for a test subject; (d) evaluating the test data using the electronic representation of the classifier and/or an ensemble of classifiers as described herein; and (e) outputting a classification of the test subject's sleep stage and/or quality based on the evaluating step. The test subject may be the same as the human subject used for training purposes (e.g., a baseline may be established for an individual using past data). In some aspects, the system will instead be trained with sensor data and/or biometric data obtained from a plurality of human subjects (e.g., a population which may contain healthy individuals known not to have OSA or CSA, individuals known to have OSA or CSA, or a combination thereof).

In another embodiment, the disclosure provides a method of classifying test data, the test data comprising sensor data and/or biometric data for a test subject, comprising: (a) accessing an electronically stored set of training data vectors, each training data vector or k-tuple representing an individual human subject and comprising sensor data and/or biometric data for the respective human subject for each replicate, the training data further comprising a classification with respect to sleep stage and/or sleep quality for the respective human subject; (b) using the electronically stored set of training data vectors to build a classifier and/or ensemble of classifiers; (c) receiving test data comprising a plurality of sensor data and/or biometric data for a human test subject; (d) evaluating the test data using the classifier(s); and (e) outputting a classification as to the sleep stage and/or sleep quality of the human test subject based on the evaluating step. Alternatively, all (or any combination of) the replicates may be averaged to produce a single value. Outputting in accordance with this invention includes displaying information regarding the classification of the human test subject in an electronic display in human-readable form. The sensor data and/or biometric data may comprise data in accordance with any of the exemplary aspects of the present systems and methods described herein. In some aspects, the set of training vectors may comprise at least 20, 25, 30, 35, 50, 75, 100, 125, 150, or more vectors.

Classifier-Based Systems and Methods

As explained above, the systems and methods provided herein may be used to determine whether SDB is likely to occur in a subject. The OSA and CSA stimulation systems according to the disclosure possess several advantages compared to prior systems, and in particular allow for more accurate tailoring of stimulation based parameters, and power savings (e.g., components of the OSA/CSA stimulation system may be disabled or switched to a low-power mode when a subject is found to be awake or in a sleep stage wherein stimulation is reduced or unnecessary). Moreover, the present systems are advantageous in that they do not require invasive or uncomfortable sensors, improving the likelihood of patient compliance and positive therapeutic outcomes.

Prior systems based on EEG and electrooculography ("EOG") provide a reliable way to detect wakefulness and sleep stage. However, such systems requires many wires and instrumentation that can interfere with sleep. In contrast, the stimulation systems according to the disclosure may are able to detect sleep stage and wakefulness in order to be able to automatically start and stop (or otherwise modulate) treatment and to determine sleep quality. The paper "Respiratory rate variability in sleeping adults without obstructive sleep apnea" (G. Gutierrez et al, Physiol. Rep., 4:17, 2016) (hereinafter, "Gutierrez 2016") describes an approach for using nasal cannula pressure respiration rate variability to determine wakefulness. However, this approach requires the use of a nasal cannula or nasal thermistor, which can also impede sleep. Moreover, the technique described in Gutierrez 2016 requires computation of fast Fourier transformations ("FFTs," a processor-intensive calculation) and only produce a sleep stage prediction every 2.7 seconds.

One simple example of determining a probabilistic function that can decide when to raise the readiness alertness, power level, or simply activate the device to treat OSA and/or CSA would be to correlate the likelihood of OSA and CSA measured during a study with the sleep stage that the subject was in. There are several wearable devices on the market that use HR detection and other inputs to determine the current sleep stage that a subject is in. For most subjects, OSA is most common during REM sleep. The sleep study may confirm if OSA is more likely during REM for the subject in question, using their sleep stage wearable and detected events, and then the system can use the sleep stage wearable to determine when the subject is in REM and either activate their OSA/CSA implanted stimulation system or otherwise raise its level of alertness. This is a simple example of a single explanatory variable determining the state of the treatment system. As more explanatory variables are added, more complex algorithms can be used that should result in more accurate predictive capabilities. As well, potential explanatory variables that do not improve predictive capability can be discarded.

In this exemplary embodiment, the implanted stimulation system 200 comprises a housing that includes both the IPG 1 and a controller configured to handle signal processing and storage, operation of the stimulation system 200, and wireless communication between the stimulation system 200 and a user application 5*a* executed on the external controller 5. The stimulation system 200 further includes a stimulating cuff electrode 2*a* located distally or proximally on the HGN to deliver stimulation to the HGN which innervates one or more upper airway muscles of the human subject for OSA relief and a stimulating lead 3*a* in the pericardiophrenic vein adjacent to the PN to deliver stimulation to the PN to treat CSA. As described herein, the system 200 may be configured to determine that SDB is likely to occur in a near term time horizon in the subject based on the sensor data received from the internal (not shown) or external sensors 4. Accordingly, based on the determination that SDB is likely to occur, the system 200 is further configured to: command the first lead to deliver a stimulation signal to the HGN through the electrode(s) 2*a* to relieve OSA, and command the second lead 3*a* to deliver an inspiration stimulation to the PN to treat CSA, wherein the first lead is commanded to deliver a stimulation signal to stimulate the HGN that is synchronized in some aspect to the respiration pace driven by the inspiration stimulation signal from the second lead. In alternative aspects, the determination that SDB is likely to occur in a near term time horizon may be performed by an external system controller 5 or by a local, remote, or cloud-based server (e.g., it may be advantageous to offload the computation required for a prediction and/or classification to an external device, rather than using the power and limited processing capabilities of an implanted controller).

It should be understood that any component or element of the system could be implanted within the body, or effected from outside the body (including stimulation), or, in the case of biomarker levels, may be the result of a sample taken from the body. The controller could be part of the implanted system or outside of the body or both, and the algorithm governing control could reside inside the body (IPG 1), outside the body on a physical device (external controller 5), and/or in the cloud.

In some aspects, the implanted controller may be configured to determine when SDB is likely using machine learning algorithms (or classifications) executed by the implanted controller (e.g., shown in FIG. 2). The classifications may use sensor data collected from any number of implanted or external sensors, using any of the techniques described herein to predict when SDB is likely to occur. In alternative aspects, the predictions and/or classifications may also be separately performed by an external controller (e.g., as shown in FIG. 2) or separately by a local, remote, or cloud-based server. It may be advantageous to offload the computation required for a prediction/classification to an external device or server—rather than using the power and limited processing capabilities of an implanted controller.

In alternative aspects, the data processing (e.g., applying machine learning) may be performed by an implanted controller (e.g., of an implantable stimulation system). However, in some aspects, power and processing resources may be leveraged more efficiently when this determination is offloaded to an external controller (e.g., an external electronic device, whether local, remote or cloud-based).

It should be understood that multiple permutations and combinations of the elements disclosed above can be used to effect treatment of sleep apnea and comorbidities. It should be further understood that this complex system of multiple targets, multiple sensors, controller(s), and machine learning could be used to treat a number of other medical conditions, especially those where there are common comorbidities and/or multiple treatment targets for the secondary indication (i.e. diabetes, heart failure, hypertension, obesity, atrial fibrillation, etc.). It should also be understood that the ability to monitor and treat co-morbidities does not require a device that addresses CSA and OSA together, but could also be implemented in a system or device that is intended to treat just one of CSA or OSA.

It should be noted that the listed machine learning algorithms, targets and comorbidities are not meant to be an exhaustive list, but are merely illustrative.

Figure 3:
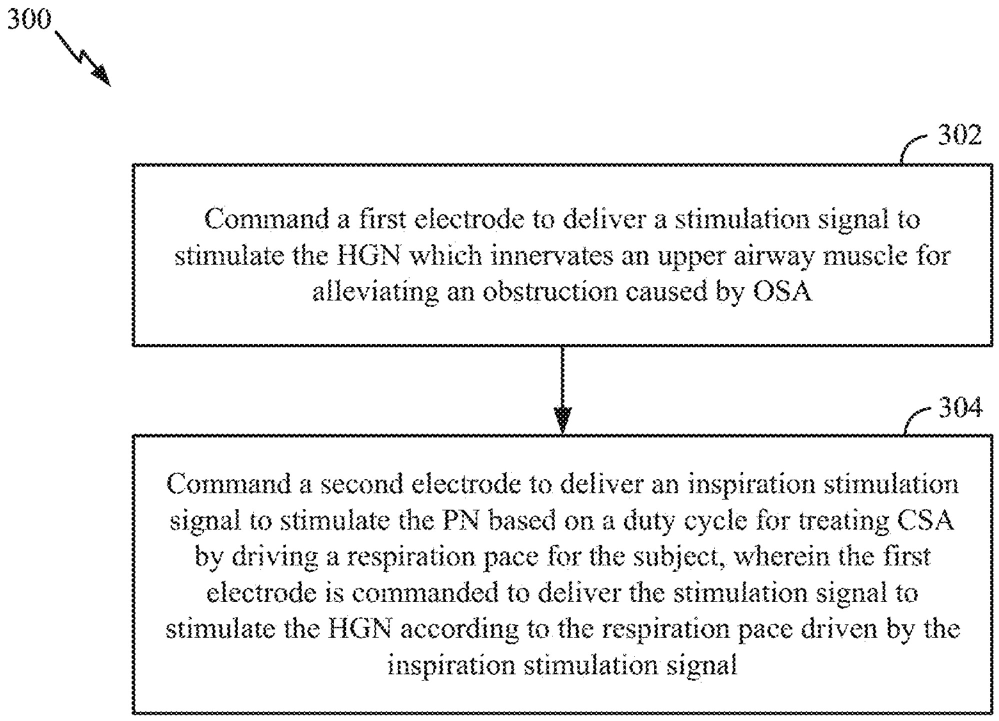
FIGS. 3-7 are conceptual flowcharts summarizing methods for treating both OSA and CSA for a human subject using the systems described herein. The flowcharts consist of at least treating both CSA and OSA in the subject by pacing breathing of the subject with PN nerve stimulation and treating OSA by timing the HGN stimulation according to the breathing pace.

FIG. 3 is a conceptual flowchart summarizing a method for treating CSA and OSA in a subject. According to various different aspects, one or more of the illustrated blocks of method 300 may be omitted, transposed, and/or contemporaneously performed. The method allows a system (e.g., the systems 100, and 200 shown in FIGS. 1-2) to treat both CSA and OSA in the subject by stimulating the PN to drive inspiration to drive the breathing pace of the subject to treat CSA and stimulating the HGN to alleviate OSA synchronized in some aspect to the paced breathing.

The method 300 may be performed by a system, as described above. In some implementations, the method 300 is performed by processing logic, including hardware, firmware, software, or a combination thereof. In some implementations, the method 300 is performed by a processor executing code stored in a non-transitory computer-readable medium (e.g., a memory).

A system performing the method 300 may include an IPG coupled to a first electrode or plurality of electrodes (e.g., the stimulating cuff electrode 2*a* shown in FIGS. 1-2) and a second electrode or plurality of electrodes (e.g., the stimulating lead 3*a* shown in FIGS. 1-2). The first electrode may be configured to stimulate a HGN of the subject and the second electrode may be configured to stimulate a PN of the subject.

At block 302, the method 300 includes commanding a first electrode to deliver a stimulation signal to stimulate the HGN which innervates at least one upper airway muscle for alleviating an obstruction caused by OSA. For example, referring back to FIGS. 1-2, the IPG 1 is coupled to an HGN lead 2 to drive a cuff electrode or plurality of electrodes 2*a* inside the cuff to deliver stimulation to a HGN which innervates at least one upper airway muscle of the subject.

At block 304, the method 300 includes commanding a second electrode to deliver an inspiration stimulation signal to stimulate the PN based on a duty cycle for treating CSA by driving a respiration pace for the subject. The first electrode may be commanded to deliver the stimulation signal to stimulate the HGN according to the respiration pace driven by the inspiration stimulation signal. For example, referring back to FIGS. 1-2, the IPG 1 is coupled to a CSA lead 3 to deliver stimulation to multiple locations of the PN of the subject.

In some aspects, the method 300 includes commanding the first electrode to deliver the stimulation signal to the HGN 0 to 500 milliseconds before commanding the second electrode to deliver the inspiration stimulation signal to a diaphragm via the PN or motor point to produce inspiration. In some aspects, both the first electrode is commanded to deliver the stimulation to the HGN and the second electrode is commanded to deliver the inspiration stimulation signal to the PN to treat CSA without detection or classification of an apneic event or hypopnea event.

Figure 4:
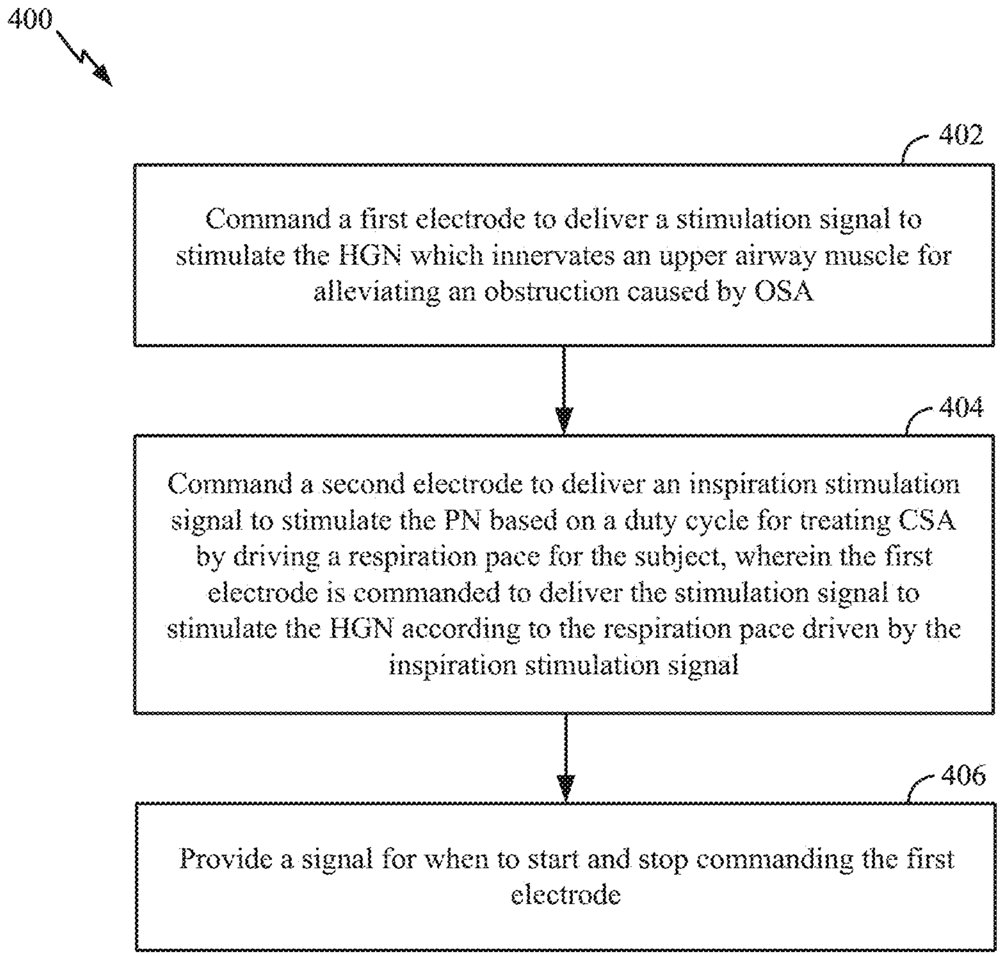

FIG. 4 is a conceptual flowchart summarizing another method for treating CSA and OSA in a subject. According to various different aspects, one or more of the illustrated blocks of method 400 may be omitted, transposed, and/or contemporaneously performed. The method allows a system (e.g., the system 100 shown in FIGS. 1 and 2) to treat both CSA and OSA in the subject by stimulating the PN to drive inspiration to drive the breathing pace of the subject to treat CSA and stimulating the HGN to alleviate OSA according to the breathing pace The method 400 may be performed by a system, as described above. In some implementations, the method 400 is performed by processing logic, including hardware, firmware, software, or a combination thereof. In some implementations, the method 400 is performed by a processor executing code stored in a non-transitory computer-readable medium (e.g., a memory).

At block 402, the method 400 includes commanding a first electrode to deliver a stimulation signal to stimulate the HGN which innervates at least one upper airway muscle for alleviating an obstruction caused by OSA. For example, referring back to FIGS. 1-2, the IPG 1 is coupled to an HGN lead 2 to drive a cuff electrode or plurality of electrodes 2*a* inside the cuff to deliver stimulation to a HGN which innervates at least one upper airway muscle of the subject.

At block 404, the method 400 includes commanding a second electrode to deliver an inspiration stimulation signal to stimulate the PN based on a duty cycle for treating CSA by driving a respiration pace for the subject. The first electrode may be commanded to deliver the stimulation signal to stimulate the HGN according to the respiration pace driven by the inspiration stimulation signal. For example, referring back to FIGS. 1-2, the IPG 1 is coupled to a CSA lead 3 to deliver stimulation to multiple locations of the PN of the subject.

At block 406, the method 400 includes providing a signal for when to start and stop commanding the first electrode. This results in turning on stimulation when it is determined that sleep disordered breathing is impending and off when SDB is no longer considered a risk, in order to save power consumption for the device. This may also help the subject be more comfortable (i.e. be less likely to be aroused from sleep) since stimulation is not occurring all the time.

Figure 5:
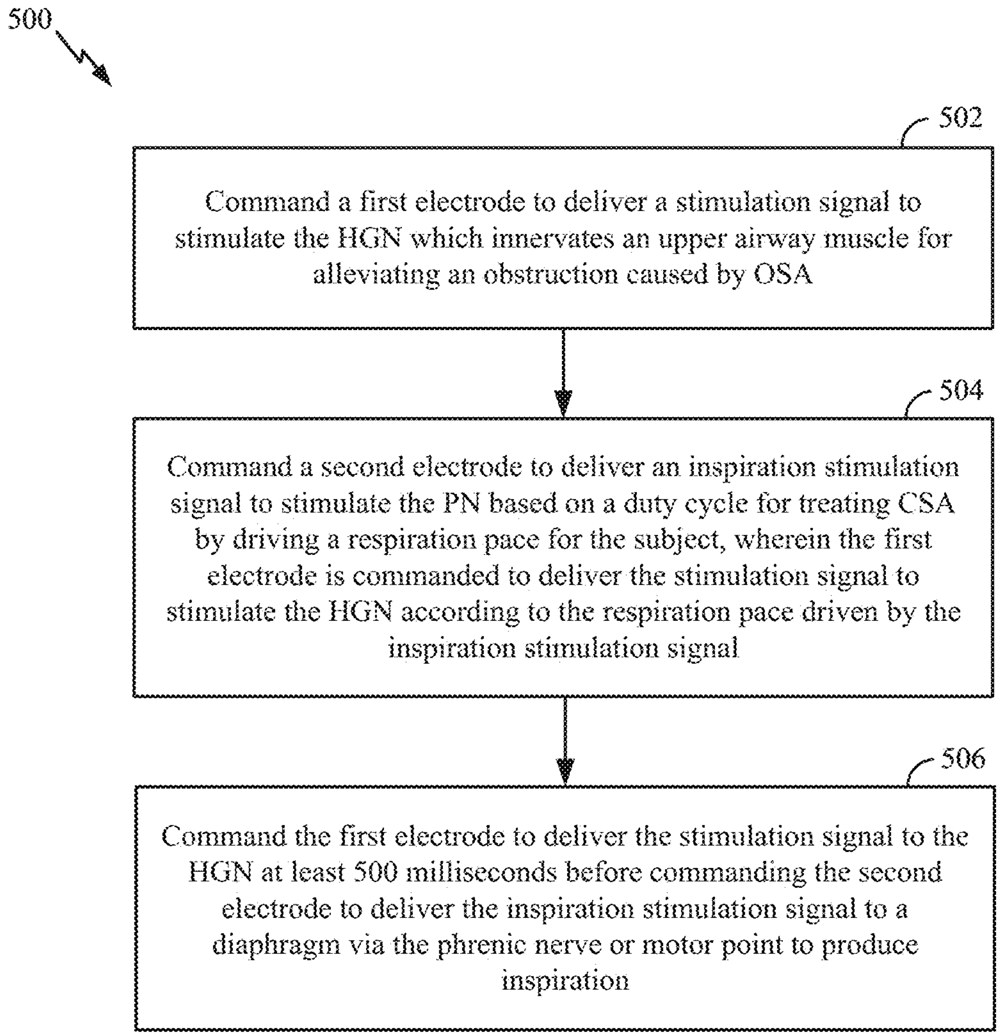

FIG. 5 is a conceptual flowchart summarizing another method for treating CSA and OSA in a subject. According to various different aspects, one or more of the illustrated blocks of method 500 may be omitted, transposed, and/or contemporaneously performed. The method allows a system (e.g., the system 100 shown in FIGS. 1 and 2) to treat both CSA and OSA in the subject by stimulating the PN to drive inspiration to drive the breathing pace of the subject to treat CSA and stimulating the HGN to alleviate OSA according to the breathing pace.

The method 500 may be performed by a system, as described above. In some implementations, the method 500 is performed by processing logic, including hardware, firmware, software, or a combination thereof. In some implementations, the method 500 is performed by a processor executing code stored in a non-transitory computer-readable medium (e.g., a memory).

At block 502, the method 500 includes commanding a first electrode to deliver a stimulation signal to stimulate the HGN which innervates at least one upper airway muscle for alleviating an obstruction caused by OSA. For example, referring back to FIGS. 1-2, the IPG 1 is coupled to an HGN lead 2 to drive a cuff electrode or plurality of electrodes 2*a* inside the cuff to deliver stimulation to a HGN which innervates at least one upper airway muscle of the subject.

At block 504, the method 500 includes commanding a second electrode to deliver an inspiration stimulation signal to stimulate the PN based on a duty cycle for treating CSA by driving a respiration pace for the subject. The first electrode may be commanded to deliver the stimulation signal to stimulate the HGN according to the respiration pace driven by the inspiration stimulation signal. For example, referring back to FIGS. 1-2, the IPG 1 is coupled to a CSA lead 3 to deliver stimulation to multiple locations of the PN of the subject.

At block 506, the method 500 includes commanding the first electrode to deliver the stimulation signal to the HGN within 500 milliseconds before commanding the second electrode to deliver the inspiration stimulation signal to a diaphragm via the phrenic nerve or motor point to produce inspiration. For example referring back to FIGS. 1-2, the IPG 1 may instruct the HGN lead 2 to drive the cuff electrode 2*a* to deliver stimulation to a HGN within 500 milliseconds before instructing the CSA lead 3 to deliver the stimulation to a diaphragm via the PN to produce inspiration in the subject.

Figure 6:
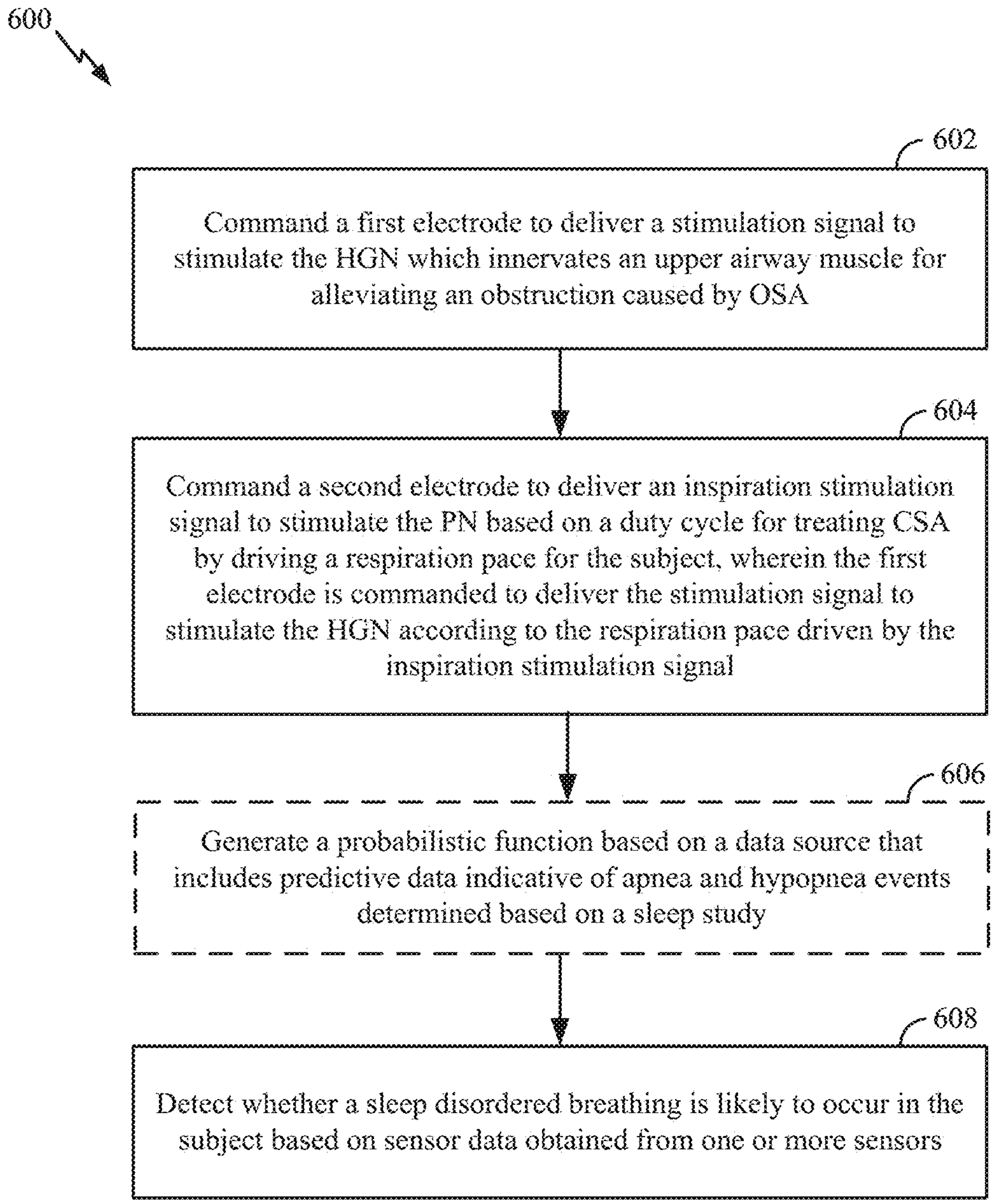

FIG. 6 is a conceptual flowchart summarizing another method for treating CSA and OSA in a subject. According to various different aspects, one or more of the illustrated blocks of method 600 may be omitted, transposed, and/or contemporaneously performed. Optional aspects are illustrated in dashed lines. The method allows a system (e.g., the system 100 shown in FIGS. 1 and 2) to treat both CSA and OSA in the subject by stimulating the PN to drive inspiration to drive the breathing pace of the subject to treat CSA and stimulating the HGN to alleviate OSA according to the breathing pace.

A system performing the method 600 may include an IPG coupled to a first electrode (e.g., the stimulating cuff electrode 2*a* shown in FIGS. 1-2) and a second electrode (e.g., the stimulating leads 3*a* shown in FIGS. 1-2) and one or more sensors. The first electrode may be configured to stimulate a HGN of the subject and the second electrode may be configured to stimulate a PN of the subject, and the one or more sensors configured to determine whether SDB is likely to occur.

The method 600 may be performed by a system, as described above. In some implementations, the method 600 is performed by processing logic, including hardware, firmware, software, or a combination thereof. In some implementations, the method 600 is performed by a processor executing code stored in a non-transitory computer-readable medium (e.g., a memory).

At block 602, the method 600 includes commanding a first electrode to deliver a stimulation signal to stimulate the HGN which innervates at least one upper airway muscle for alleviating an obstruction caused by OSA. For example, referring back to FIGS. 1-2, the IPG 1 is coupled to an HGN lead 2 to drive a cuff electrode or plurality of electrodes 2*a* inside the cuff to deliver stimulation to a HGN which innervates at least one upper airway muscle of the subject.

At block 604, the method 600 includes commanding a second electrode to deliver an inspiration stimulation signal to stimulate the PN based on a duty cycle for treating CSA by driving a respiration pace for the subject. The first electrode may be commanded to deliver the stimulation signal to stimulate the HGN according to the respiration pace driven by the inspiration stimulation signal. For example, referring back to FIGS. 1-2, the IPG 1 is coupled to a CSA lead 3 to deliver stimulation to multiple locations of the PN of the subject.

Optionally, at block 606, the method 600 includes generating a probabilistic function based on a data source that includes predictive data indicative of apnea and hypopnea events determined based on a sleep study or some other source of predictive data. The probabilistic function may be generated or tuned based on machine learning algorithms. SDB may be determined likely to occur in the near term time horizon in the subject based on the probabilistic function. In some aspects, a determination that SDB is likely to occur may be determined using probabilistic indicators corresponding to one or more of blood oxygen level, blood pressure, heart rate, heart rate variability, electrocardiogram (ECG) data, electroencephalogram (EEG) data, electromyography (EMG) results, impedance, cardiothoracic impedance, sleep state, accelerometer data, or auscultation, and combinations thereof. For example, referring back to FIG. 2., generating the probabilistic function may be generated or tuned on an external system controller 5.

At block 608, the method 600 includes detecting whether a SDB is likely to occur in the subject based on sensor data obtained from one or more sensors. The second electrode may be commanded to deliver the inspiration stimulation signal to the PN based on a determination that a SDB is likely to occur in the subject based on the sensor data. For example, referring back to FIG. 2., detecting whether the SDB is likely to occur in the subject may be performed on an external system controller 5.

In some aspects, the one or more sensors include a microphone configured to determine information indicative of snoring, wherein the SDB is determined likely to occur in the subject based on a presence of snoring. In some aspects, the one or more sensors include an inertial sensor configured to determine body position of the subject, wherein the SDB is determined likely to occur in the subject based on a determination that the body position of the subject. In some aspects, the one or more sensors include a heart rate sensor configured to determine heart rate of the subject, wherein the SDB is determined likely to occur in the subject based on a determination that the heart rate of the subject is slow. In some aspects, the one or more sensors are configured to determine sleep stages, wherein the SDB is determined likely to occur in the subject based on a determination that the subject is in a rapid eye movement (REM) stage. In some aspects, the one or more sensors include a electromyography sensor (EMG) configured to detect signals generated by muscles of a subject, wherein the SDB is determined likely to occur in the subject based on a determination that the detected signals sent from the PN to a diaphragm are waning. For example, referring back to FIG. 2., the sensor data may be collected from various sensors comprising the external sensor 4 (e.g., wrist worn sensor).

Figure 7:
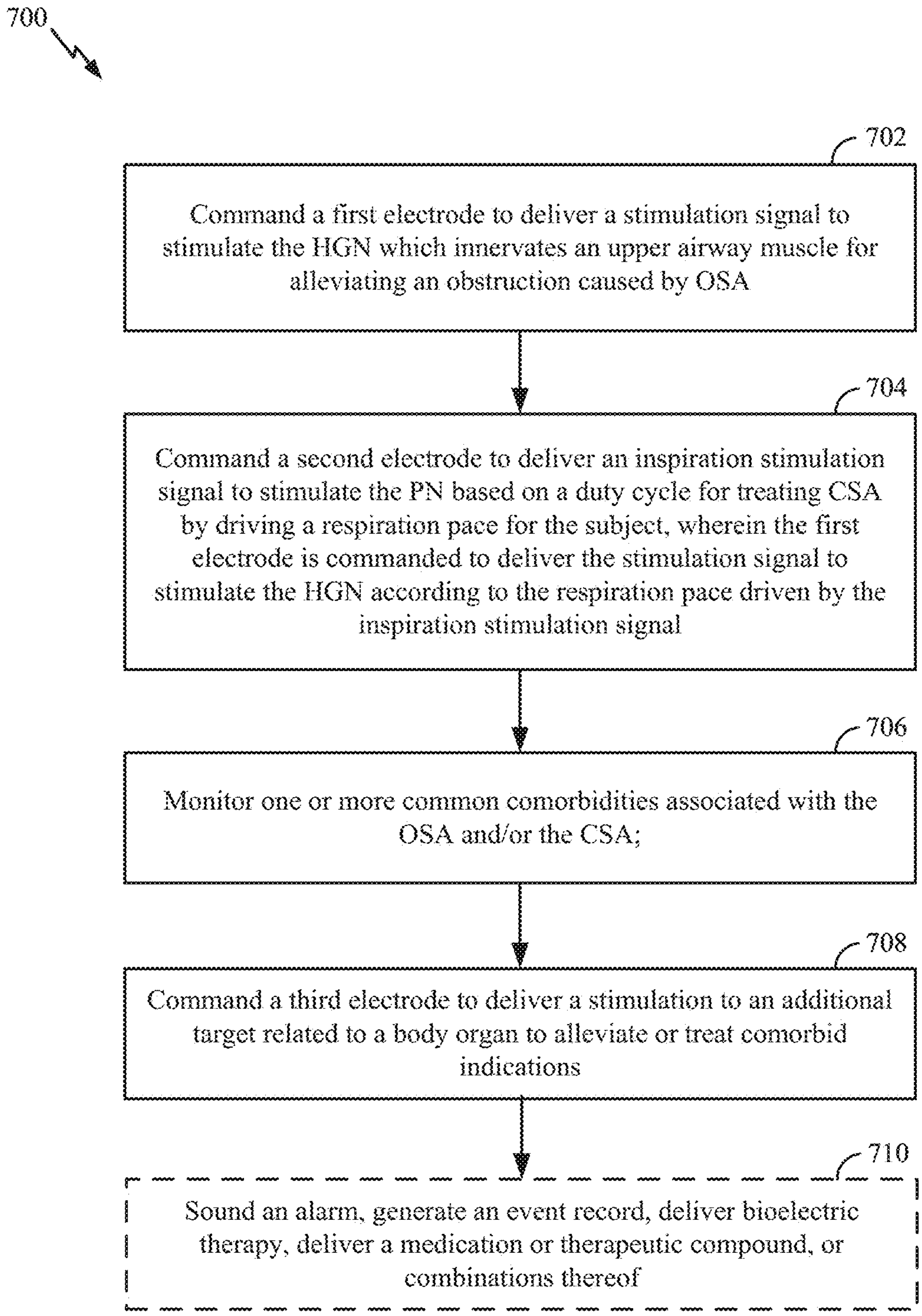

FIG. 7 is a conceptual flowchart summarizing another method for treating CSA and OSA in a subject, while also monitoring and/or treating one or more comorbidities associated with SDB. According to various different aspects, one or more of the illustrated blocks of method 700 may be omitted, transposed, and/or contemporaneously performed. Optional aspects are illustrated in dashed lines. The method 700 allows a system (e.g., the systems 100, and 200 shown in FIGS. 1-2) to treat both CSA and OSA in the subject by stimulating the PN to drive inspiration to drive the breathing pace of the subject to treat CSA and stimulating the HGN to alleviate OSA according to the breathing pace.

A system performing the method 700 may include an IPG coupled to a first electrode (e.g., the stimulating cuff electrode 2*a* shown in FIGS. 1-2), a second electrode (e.g., the stimulating leads 3*a* shown in FIGS. 1-2), and a third electrode. The first electrode may be configured to stimulate a HGN of the subject, the second electrode may be configured to stimulate a PN of the subject, and the third electrode may be configured to stimulate an additional target related to a body organ of the subject.

The method 700 may be performed by a system, as described above. In some implementations, the method 700 is performed by processing logic, including hardware, firmware, software, or a combination thereof. In some implementations, the method 700 is performed by a processor executing code stored in a non-transitory computer-readable medium (e.g., a memory).

At block 702, the method 700 includes commanding a first electrode to deliver a stimulation signal to stimulate the HGN which innervates at least one upper airway muscle for alleviating an obstruction caused by OSA. For example, referring back to FIGS. 1-2, the IPG 1 is coupled to an HGN lead 2 to drive a cuff electrode or plurality of electrodes 2*a* inside the cuff to deliver stimulation to a HGN which innervates at least one upper airway muscle of the subject.

At block 704, the method 700 includes commanding a second electrode to deliver an inspiration stimulation signal to stimulate the PN based on a duty cycle for treating CSA by driving a respiration pace for the subject. The first electrode may be commanded to deliver the stimulation signal to stimulate the HGN according to the respiration pace driven by the inspiration stimulation signal. For example, referring back to FIGS. 1-2, the IPG 1 is coupled to a CSA lead 3 to deliver stimulation to multiple locations of the PN of the subject.

At block 706, the method 700 includes monitoring one or more common comorbidities associated with the OSA and/or the CSA. The method may include monitoring and/or stimulating targets (including those unrelated to OSA or CSA) to treat underlying conditions which are frequently comorbid with OSA or CSA either by using the same IPG or in concert with one or more additional IPGs and/or external stimulators. For instance, some of the underlying conditions associated with OSA or CSA may include heart failure, atrial fibrillation, stroke, kidney failure, hypertension, obesity, and diabetes.

At block 708, the method 700 includes commanding the third electrode on a third lead to deliver a stimulation to the additional target related to the body organ to alleviate or treat comorbid indications. The additional body organ may be one of a carotid baroreceptor, a vagus nerve, a target on or near a heart, a target on or near a liver, a target on or near a pancreas, a carotid sinus, or a target on or near a stomach of the subject. It should be understood that other targets associated with conditions comorbid to OSA and CSA are also possible.

Accordingly, the method may have the capability to stimulate the additional targets to alleviate or treat comorbid indications (which may also, but not necessarily, alleviate sleep apnea). For instance, the method may also stimulate other targets related to a body organ such as the laryngeal nerve, or motor end points, and muscles such as the diaphragm and the heart to provide relief from OSA and/or CSA. Some other targets related to a body organ may include carotid baroreceptors, and/or vagus nerve for heart failure, the heart for atrial fibrillation, the stomach for gastric pacing, or the liver, pancreas, vagus nerve, gut, and/or carotid sinus for diabetes.

Optionally, at block 710, the method 700 includes sounding an alarm, generating an event record, delivering bioelectric therapy, delivering a medication or therapeutic compound (not necessarily via the system), or combinations thereof, based on the sensor data being determined to be indicative of one or more of atrial fibrillation, acute heart failure, reduced blood oxygen levels, elevated glucose levels, and combinations thereof. For example, referring back to FIG. 2., an alarm may be triggered on either the external system controller 5 or on the external sensor 4, and/or remotely for a healthcare provider via a cloud based application.

It is understood that the method illustrated by FIGS. 4-7 are exemplary in nature and that the steps described herein may be combined to generate alternative embodiments.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A system for treatment of Central Sleep Apnea (CSA) and Obstructive Sleep Apnea (OSA) in a subject, comprising:
- an implantable pulse generator (IPG) coupled to a first electrode and a second electrode, wherein the first electrode is configured to stimulate a hypoglossal nerve (HGN) of the subject and the second electrode is configured to stimulate a phrenic nerve (PN) of the subject; and
- a controller comprising a processor and memory, communicatively linked to the IPG and configured to:
  - command the first electrode to deliver a stimulation signal to stimulate the HGN which innervates an upper airway muscle for alleviating an obstruction caused by OSA, and
  - command the second electrode to continuously deliver an inspiration stimulation signal to stimulate the PN on a duty cycle for treating CSA by proactively driving a respiration pace for the subject, wherein the first electrode is commanded to deliver the stimulation signal to stimulate the HGN according to the respiration pace driven by the inspiration stimulation signal.

2. The system of claim 1, wherein the controller derives, from the duty cycle of the inspiration stimulation signal when to start and stop commanding the first electrode to deliver the stimulation signal to stimulate the HGN.

3. The system of claim 1, wherein the controller is further configured to:
- command the first electrode to deliver the stimulation signal to the HGN within 500 milliseconds before commanding the second electrode to deliver the inspiration stimulation signal to a diaphragm via the PN or motor point of the diaphragm to produce inspiration.

4. The system of claim 1, wherein both the first electrode is commanded to deliver the stimulation to the HGN and the second electrode is commanded to deliver the inspiration stimulation signal to the PN to treat CSA without detection or classification of an apneic event.

5. The system of claim 1, wherein the controller is further configured to:
- detect whether a sleep disordered breathing (SDB) is likely to occur in the subject based on sensor data obtained from one or more sensors, wherein the second electrode is commanded to deliver the inspiration stimulation signal to the PN based on a determination that the SDB is likely to occur in the subject based on the sensor data.

6. The system of claim 5, wherein the one or more sensors include a microphone configured to determine information indicative of snoring, wherein the SDB is determined likely to occur in the subject based on a presence of snoring.

7. The system of claim 5, wherein the one or more sensors include an inertial sensor configured to determine body position of the subject, wherein the SDB is determined likely to occur in the subject based on a determination that the body position of the subject is laying facing supine.

8. The system of claim 5, wherein the one or more sensors include a heart rate sensor configured to determine heart rate of the subject, wherein the SDB is determined likely to occur in the subject based on a determination that the heart rate of the subject is slow.

9. The system of claim 5, wherein the one or more sensors are configured to determine sleep stages, wherein the SDB is determined likely to occur in the subject based on a determination that the subject is in a rapid eye movement (REM) stage.

10. The system of claim 5, wherein the one or more sensors include an electromyography sensor (EMG) configured to detect signals generated by muscles of a subject, wherein the SDB is determined likely to occur in the subject based on a determination that the detected signals sent from the PN to a diaphragm are waning.

11. The system of claim 5, wherein the controller is further configured to:

generate a probabilistic function based on a data source that includes predictive data indicative of apnea and hypopnea events determined based on a sleep study, wherein the probabilistic function is generated or tuned based on machine learning algorithms, wherein the SDB is determined likely to occur in the subject based on the probabilistic function.

12. The system of claim 11, wherein a determination that SDB is likely to occur is further determined using probabilistic indicators corresponding to one or more of blood oxygen level, blood pressure, heart rate, heart rate variability, electrocardiogram (ECG) data, electroencephalogram (EEG) data, electromyography (EMG) results, impedance, cardiothoracic impedance, sleep state, accelerometer data, or auscultation, and combinations thereof.

13. The system of claim 1, wherein the IPG is further coupled to a third electrode, wherein the third electrode is configured to stimulate an additional target related to a body organ of the subject, wherein the controller is further configured to:

monitor one or more common comorbidities associated with the OSA and/or the CSA; and command the third electrode to deliver a stimulation to the additional target related to the body organ to alleviate or treat comorbid indications, wherein the additional body organ is one of a carotid baroreceptor, a vagus nerve, a target on or near a heart, a target on or near a liver, a target on or near a pancreas, a carotid sinus, or a target on or near a stomach of the subject.

14. The system of claim 13, wherein the system further comprises one or more sensors configured to determine sensor data indicative of one or more of atrial fibrillation, acute heart failure, reduced blood oxygen levels, elevated glucose levels, and combinations thereof, wherein the controller is further configured to sound an alarm, generate an event record, deliver bioelectric therapy, deliver a medication or therapeutic compound, or combinations thereof, based on the sensor data being determined to be indicative of one or more of atrial fibrillation, acute heart failure, reduced blood oxygen levels, elevated glucose levels, and combinations thereof.

15. A method for treatment of Central Sleep Apnea (CSA) and Obstructive Sleep Apnea (OSA) in a subject, comprising:

delivering, via a first electrode that is part of an implantable pulse generator (IPG), a stimulation signal to stimulate a hypoglossal nerve (HGN) of the subject which innervates an upper airway muscle for alleviating an obstruction caused by OSA; and continuously delivering, via a second electrode that is part of the IPG, an inspiration stimulation signal to stimulate a phrenic nerve (PN) on a duty cycle for treating CSA by proactively driving a respiration pace for the subject, wherein the first electrode delivers the stimulation signal to stimulate the HGN according to the respiration pace driven by the inspiration stimulation signal.

16. The method of claim 15, wherein a timing for when to start and stop delivering the stimulation signal to stimulate the HGN via the first electrode is derived from the duty cycle of the inspiration stimulation signal.

17. The method of claim 15, further comprising:

delivering, via the first electrode, the stimulation signal to the HGN at least 500 milliseconds before delivering, via the second electrode, the inspiration stimulation signal to a diaphragm via the PN or motor point to produce inspiration.

18. The method of claim 15, wherein both the first electrode delivers the stimulation to the HGN and the second electrode delivers the inspiration stimulation signal to the PN to treat CSA without detection or classification of an apneic event.

19. The method of claim 15, further comprising:

detecting whether a SDB is likely to occur in the subject based on sensor data obtained from one or more sensors, wherein the second electrode is commanded to deliver the inspiration stimulation signal to the PN based on a determination that the SDB is likely to occur in the subject based on the sensor data.

20. The method of claim 15, further comprising:

monitoring one or more common comorbidities associated with the OSA and/or the CSA; and delivering, via a third electrode that is part of the IPG, a stimulation to an additional target related to a body organ of the subject to alleviate or treat comorbid indications, wherein the additional body organ is one of a carotid baroreceptor, a vagus nerve, a target on or near a heart, a target on or near a liver, a target on or near a pancreas, a carotid sinus, or a target on or near a stomach of the subject.

* * * * *